US012582737B1

(12) United States Patent
Palgon

(10) Patent No.: US 12,582,737 B1
(45) Date of Patent: Mar. 24, 2026

(54) FORCED FRAGRANCE DISTRIBUTION SYSTEM AND METHOD

(71) Applicant: Shmuel D. Palgon, Miami, FL (US)

(72) Inventor: Shmuel D. Palgon, Miami, FL (US)

( * ) Notice: Subject to any disclaimer, the term of this patent is extended or adjusted under 35 U.S.C. 154(b) by 492 days.

(21) Appl. No.: 18/086,573

(22) Filed: Dec. 21, 2022

Related U.S. Application Data

(60) Provisional application No. 63/292,187, filed on Dec. 21, 2021.

(51) Int. Cl.
*A61L 9/04* (2006.01)
(52) U.S. Cl.
CPC ............. *A61L 9/04* (2013.01); *A61L 2209/22* (2013.01)
(58) Field of Classification Search
CPC ........ A61L 9/04; A61L 9/127; A61L 2209/16; A61L 2209/22
USPC .................................... 261/DIG. 88, DIG. 89
See application file for complete search history.

(56) References Cited

U.S. PATENT DOCUMENTS

| | | | |
|---|---|---|---|
| 3,589,563 A | | 6/1971 | Carragan et al. |
| 4,759,501 A | * | 7/1988 | Silvenis .................... A61L 9/14 |
| | | | 239/289 |
| 5,302,359 A | * | 4/1994 | Nowatzki ................. F24F 3/12 |
| | | | 422/123 |

| | | | |
|---|---|---|---|
| 5,466,399 A | * | 11/1995 | Von Kempski ........... F24F 3/12 |
| | | | 261/DIG. 65 |
| 5,542,605 A | | 8/1996 | Campau |
| 5,756,047 A | * | 5/1998 | West ...................... B01D 50/60 |
| | | | 95/212 |
| 5,851,442 A | * | 12/1998 | Spector ..................... A61L 9/12 |
| | | | 261/DIG. 65 |
| 5,924,597 A | | 7/1999 | Lynn |
| 6,283,461 B1 | * | 9/2001 | Joshi ..................... B05B 1/3006 |
| | | | 239/533.13 |
| 6,511,531 B1 | * | 1/2003 | Cartellone .............. A61L 9/122 |
| | | | 261/DIG. 89 |
| 6,887,299 B2 | * | 5/2005 | Weigl ........................ A61L 9/12 |
| | | | 422/5 |
| 7,798,424 B2 | | 9/2010 | Lin |
| 7,854,394 B2 | | 12/2010 | Powell et al. |
| 9,435,550 B1 | * | 9/2016 | Marinelli .................. F24F 3/12 |
| 2002/0105099 A1 | * | 8/2002 | Warren ................... A61L 9/122 |
| | | | 261/26 |
| 2012/0156980 A1 | | 6/2012 | Zelicovich |

\* cited by examiner

*Primary Examiner* — Charles S Bushey
(74) *Attorney, Agent, or Firm* — Bycer & Marion, PLC; Matthew L. Bycer

(57) ABSTRACT

A vapor distribution system designed for use in low pressure environments of a forced air conditioning system. The includes use of a housing with vents, a liquid reservoir with a downward facing spray release, and a porous receptacle. The liquid reservoir and porous receptacle are both fully contained within the housing. When the system is activated, the liquid is siphoned through an upside down "U" shaped flow path into a nozzle. Liquid is then ejected in a downward spray onto the receptacle. In the low pressure within the return, the liquid evaporates off of the receptacle and diffuses through the vents into a distribution path, such as the ducts of an HVAC system via the fan blower.

18 Claims, 6 Drawing Sheets

FORCED FRAGRANCE DISTRIBUTION SYSTEM AND METHOD

CLAIM OF PRIORITY

The present application includes subject matter disclosed in and claims priority to a provisional application entitled "Scently Rocket" filed Dec. 21, 2021 and assigned Ser. No. 63/292,187, describing an invention made by the present inventor, herein incorporated by reference.

BACKGROUND OF THE INVENTION

1. Field of the Invention

The present invention relates to a device and method for dispersing airborne fragrance particles in a mess-free, efficient manner via a forced air distribution system.

2. Description of Related Prior Art

Devices for distributing fragrance particles via a forced air system are known but have significant drawbacks that have limited the appeal and widespread adoption. Currently, all devices that use an HVAC system to distribute particles do so by releasing liquid directly into the HVAC ducts, leaving a messy residue in the system and on its filter. The present invention offers a clean solution that does not dirty the HVAC system, and preserves the life of the system's air filter.

Typical air fragrance devices deposit concentrated droplets of fragrance directly into a forced central ventilation system to aromatize a space. The device contains an electronic automatic programmable dispensing device and an aerosol container filled with a fragrant liquid. Such devices are sprayed near the air filters of a forced central ventilation system. These devices have the disadvantage of depositing fragrant liquid directly into the HVAC system. They leave a messy, oily residue in the filter, and ultimately shorten the air filter's lifespan.

Also known are battery powered, mechanically activated air fresheners that discharge an aerosolized fragrance into the primary distribution duct of an HVAC system. Many of these systems rely on a piezoelectric assembly to control the frequency of fragrance discharge. Such devices also have the disadvantage of polluting the forced air system and filters with an oily residue.

Some existing systems dispense fragrances into an HVAC system in quantities large enough to spread an aroma throughout a large building. These devices consist of a plurality of containers, a plurality of means for dispensing containers, a plurality of solenoids, a plurality of programmable timers, and a single fan timer. The multiplicity of containers, dispensers, solenoids, and timers allows users to program the timers to dispense specific fragrances at selected times for selected rooms and for selected durations. Still, these systems are similar to others in that the liquid is dispensed directly into the ductwork of the building. These systems use conventional pressurized aerosol containers to release fragrance directly into the HVAC system, soiling the ducts and air filters. Unlike this system, the present device uses a novel tubing and nozzle system to strategically release the aerosolized particles into a receptacle. The vapors are then released into the HVAC system; the HVAC system and its filters remain clean and mess free.

Automatic, gravity powered devices for intermittently dispensing a liquid sometimes rely on absorbent pads to dispense liquids. But these devices do not allow the liquid to evaporate, nor do they distribute vapor. Rather, they rely on the pad to regulate flow. The liquid remains in a liquid state, and is ejected from the pad as a liquid at a particular frequency. The devices are composed of a container for holding a dispensable liquid, a flow regulator that permits liquid to flow out of the container at a controlled rate, and a timing and dispensing assembly. The timing and dispensing assembly, which can sometimes be an absorbent pad, accumulates a liquid from the flow regulator and then periodically dispenses a constant volume of liquid. The present invention is distinguishable because the device does not involve the removal of any liquid from the pad. Rather the present invention relies on low air pressure to evaporate the vapor directly from the pad.

Automatic air freshener spraying devices which dispense a uniform mist are also a known art. These devices rely on a gearing mechanism to trigger the spray release. Unlike with the present invention, such devices spray aerosolized particles directly into the air, rather onto a receptacle. Such devices do not use a nozzle or a downward facing spray release to generate a downward spray, and are not intended for use within a forced air system.

Other devices dispense aerosolized particles at timely intervals. They operate on a time interval determined by a resistor-capacitor circuit. A transistor detector-amplifier initiates a cycle of motor rotation. But, unlike the present invention, these devices release the aerosolized particles into the air. They do not concentrate them onto a receptacle. They do not use a tubing and nozzle system that allows for a focused, downward spray. These devices are intended for use in a forced air system or other low-pressure environment.

The shortcomings in conventional particle spreading systems highlight the need for the present invention. The present invention relies on a low-pressure system, such as the space between the air return and fan of a forced air system, to evaporate liquid into vapor and to then spread the vapor throughout an area. The liquid is absorbed into the receptacle, leaving the air filter and ducts clean and free of oily residues.

The present invention provides mess-free passive distribution of aerosolized or gaseous particulates in a forced air distribution system.

It is therefore an object of the present invention to provide a device with vents to allow outflow of particulates evaporated from an internal receptacle.

It is a further object of the present invention to provide a method of passively distributing fan blown particulates from within a forced air distribution system.

These and other objects of the present invention will become apparent to those skilled in the art as the description thereof proceeds.

SUMMARY OF THE INVENTION

A vapor spreading system is intended for use in forced air distribution networks. When a fragrance unit is placed into the space of an air return in a typical forced air conditioning system, such as an air return system of a forced air residential or commercial air conditioning system, preferably in the space between the air return and the fan of a forced air system, the downwind fan creates a low-pressure environment around and within the fragrance unit such that aerosolized fragrance particles are released from a receptacle, such a sponge, and exit vents in the fragrance unit housing, and thereby may pass the fan blower into the distribution (e.g., ducts) and be distributed throughout the affected zone through vents into affected rooms.

The fragrance unit may include a liquid reservoir that can be accessed and removed to allow replacement of the receptacle sponge. Fluid is drawn from an overhead reservoir (within the housing) via a curved flow path straw that allows liquid to be siphoned from the bottom of the reservoir, through a nozzle and out onto a receptacle. The curved flow path of the straw connects and provides a fluid communication path from the reservoir to a nozzle. The nozzle directs the fluid or liquid to be sprayed from the reservoir downward into the permeable receptacle. Preferably, the reservoir, and particularly the receptacle is enclosed in a ventilated housing. When the fragrance unit is placed upstream of a vacuum fan, according to the Bernoulli principle, the low-pressure environment created around the fragrance unit and housing vents causes low pressure within the fragrance unit housing and evaporation or aerosolization of the fragrance or liquids that had been absorbed in the receptacle, to evaporate into vapor within the housing unit above the receptacle. The vapor exits the housing through an array of vents to pass through the fan system and enter the duct work, and thereby spread via a distribution path to the affected area.

BRIEF DESCRIPTION OF THE FIGURES

The drawings described herein are for illustration purposes only and are not intended to limit the scope of the present disclosure in any way

DETAILED DESCRIPTION OF THE PREFERRED EMBODIMENTS

A fragrance unit preferably includes a self-contained reservoir of fragrance materials, preferably a liquid, preferably a scented or essential oil, that can be selectively, or regularly released onto a receptacle below. The fluid on the receptacle is preferably at least partially absorbed into the permeable receptacle. As the liquid evaporates or is otherwise aerosolized due to vapor pressure differences, the aerosolized fragrance particulates exit the fragrance unit housing and enter the general area of the air return or airflow network of a typical forced air conditioning system. By placing the receptacle completely within the housing, splash and other drips will be prevented, thus providing a safe and clean workable area. The fragrance unit may be moved, or removed via simply lifting and carrying away. The receptacle may be removable to allow replacement of receptacle as the receptacle either loses its permeable properties, or is otherwise oversaturated. Venting on the system is preferably hexagonal shaped, and the housing of fragrance unit is preferably shaped like a rocket, with a rounded or flattened top, vertical circumferential walls, and a widened base portion that provides both aesthetic appeal and balance (as when the reservoir is full and the center of weight is high) with widened legs.

Figure 1:
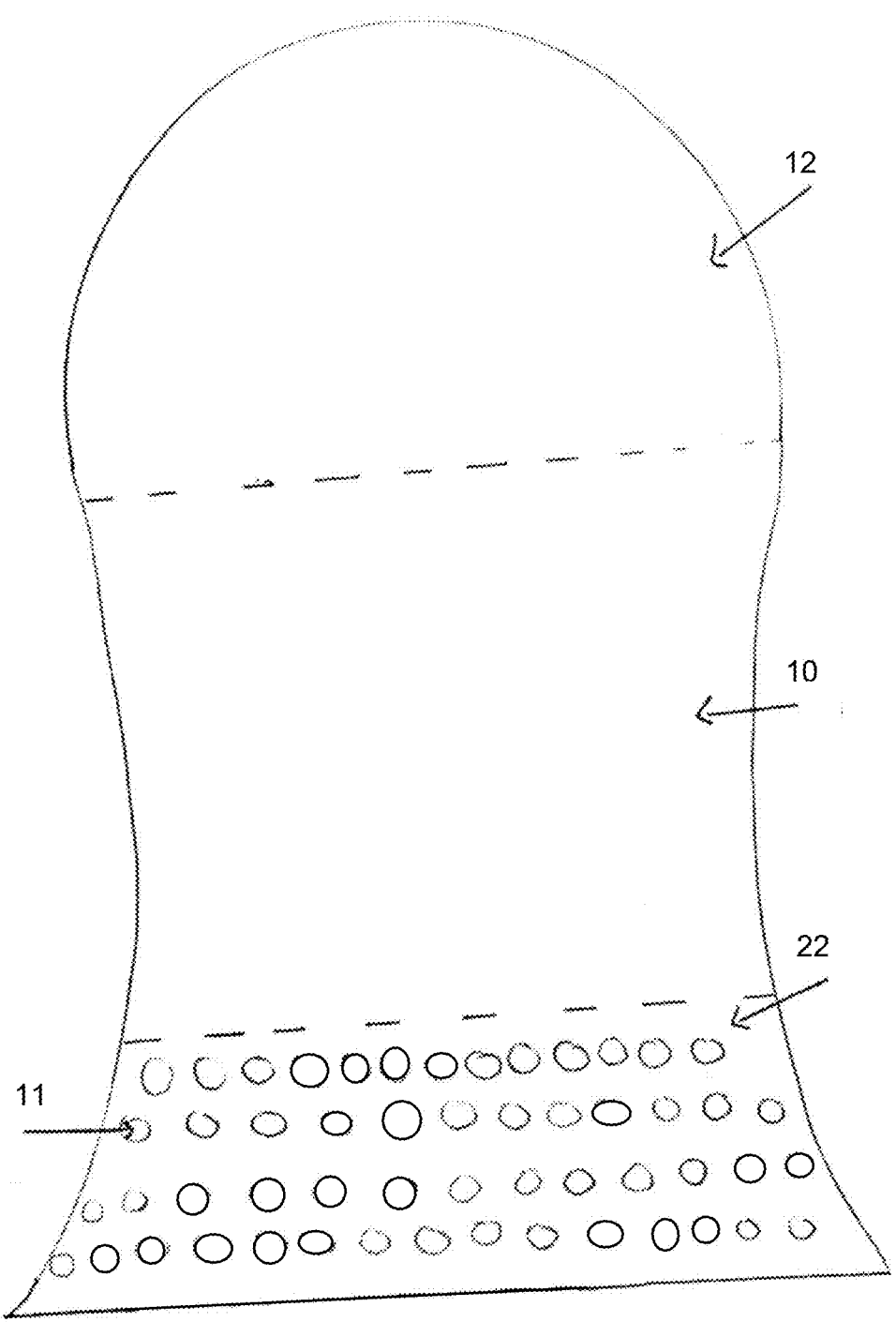
FIG. 1 is an exterior front view of the system.

A side view of the fragrance unit 9 is shown in FIG. 1. The top includes a removable housing cover 12 to access reservoir to replace and/or refill, or work on motor, or power source, such as replaceable battery. Within housing 10, the components are stored, as will be described herein. This is a representation of the diagrams and photos shown in the parent provisional patent application Ser. No. 63/292,187, incorporated by reference. Vent holes of vent 11 are set around the perimeter of the housing 10 and partial or complete removal of the bottom compartment may be opened to access, place, and replace the receptacle therein.

Figure 2:
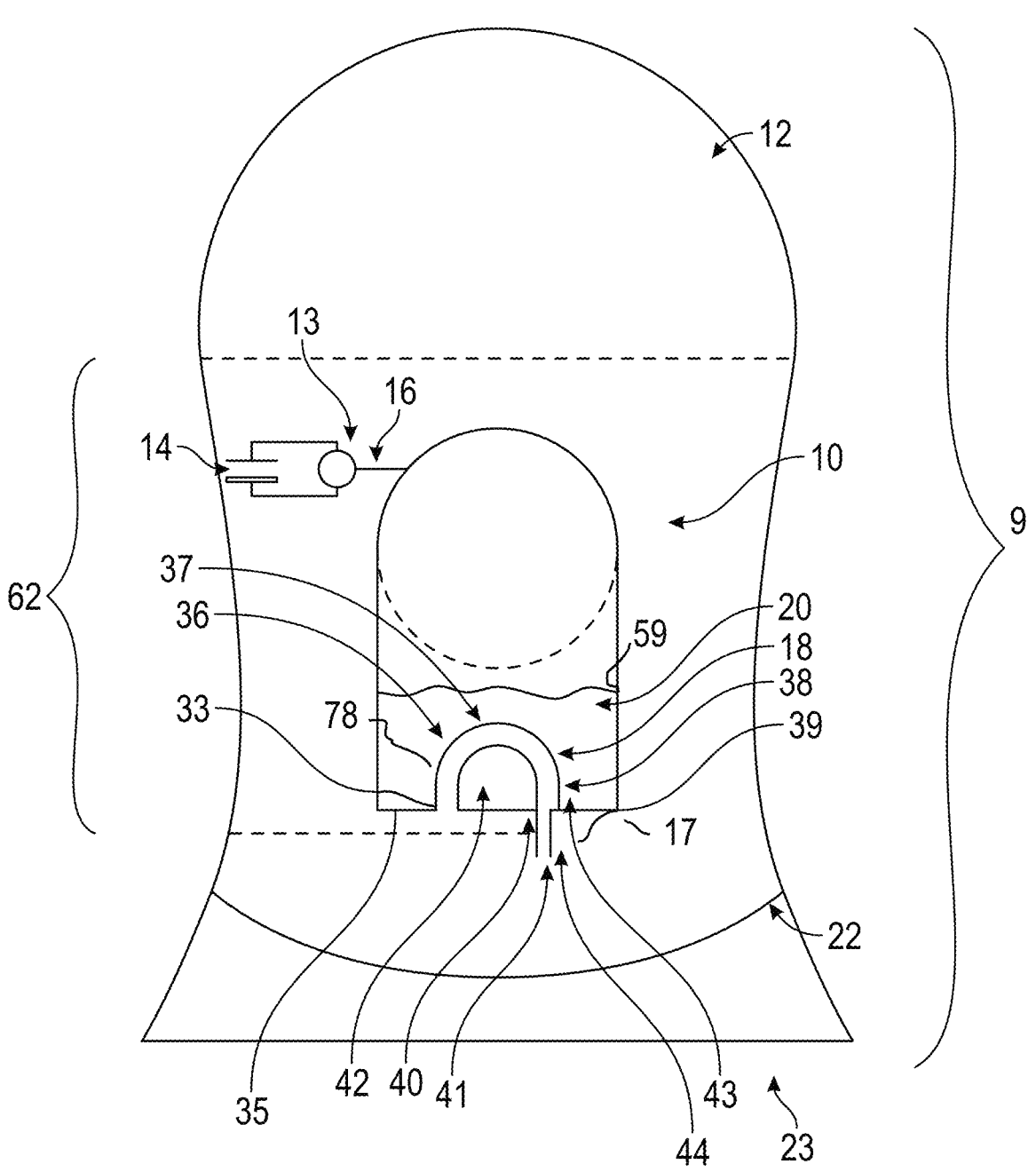
FIG. 2 is a schematic view of the system.
Figure 3:
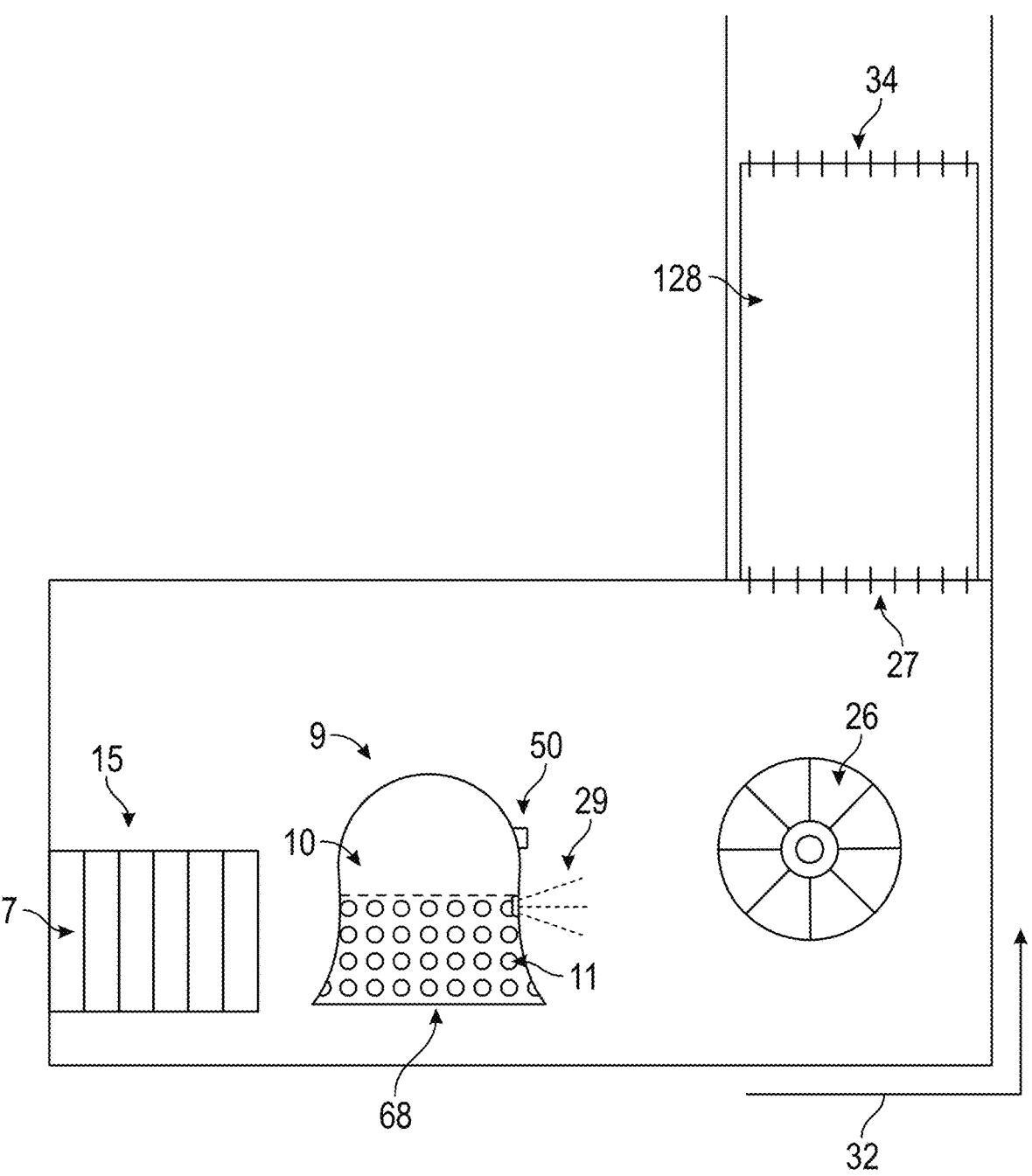
FIG. 3 is an illustrative diagram of the systems placement within a forced air system.

As shown in FIG. 2, a systematic overview of a preferred embodiment of the fragrance unit (9) comprises a housing (10) that may be stored in a low-pressure environment, such as within a forced air system (29), between the air return (15) and the fan (26) with the schematic shown in FIG. 3. The fragrance unit may include a housing (10) that encapsulates the various working components of the unit. A liquid reservoir (17), stores a liquid capable of emitting aromatic, aerosolized, or other particles and particulates that may provide conditioning or altering of the air in the system.

Figure 4:
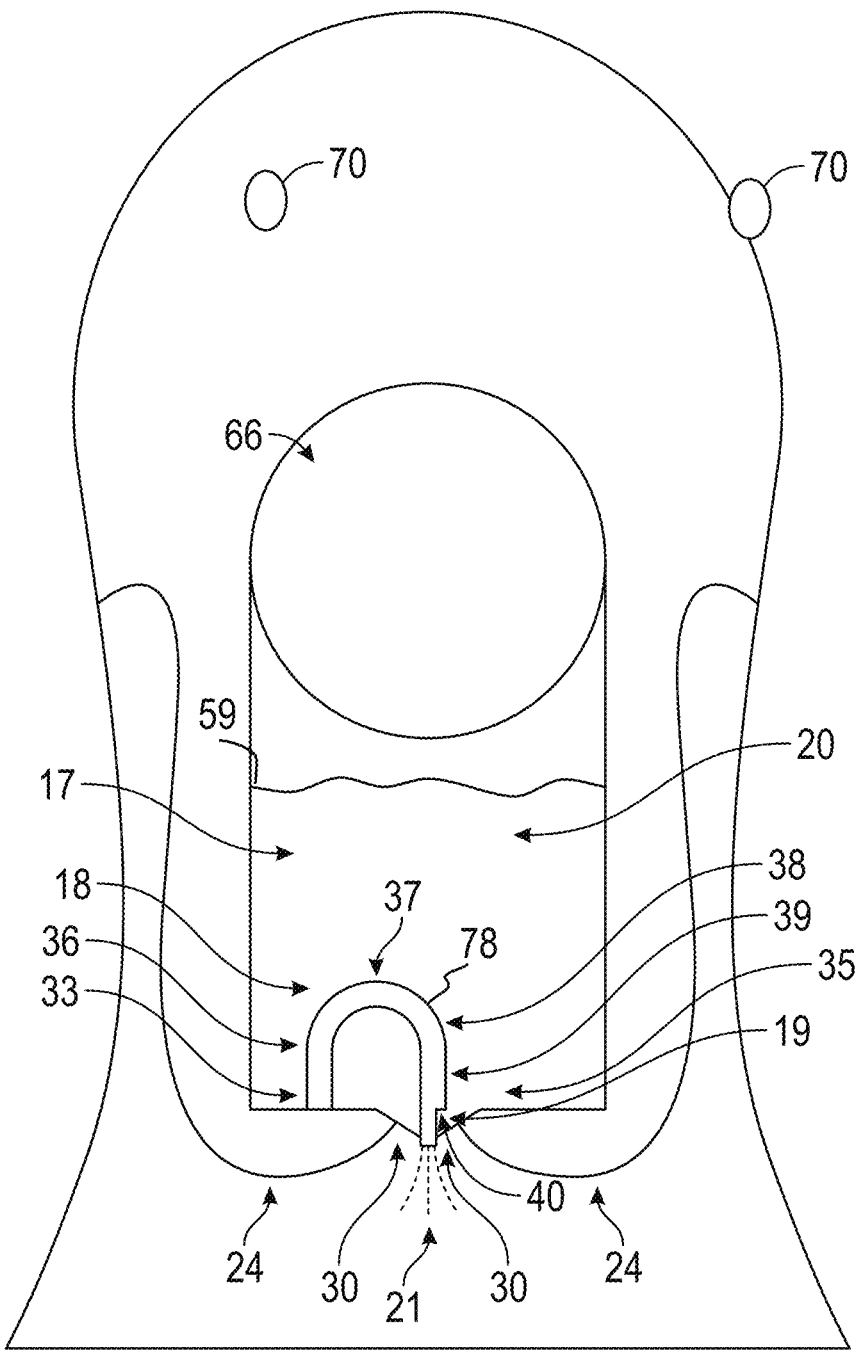
FIG. 4 is a view of the curved straw, nozzle, and spray release mechanism.
Figure 5:
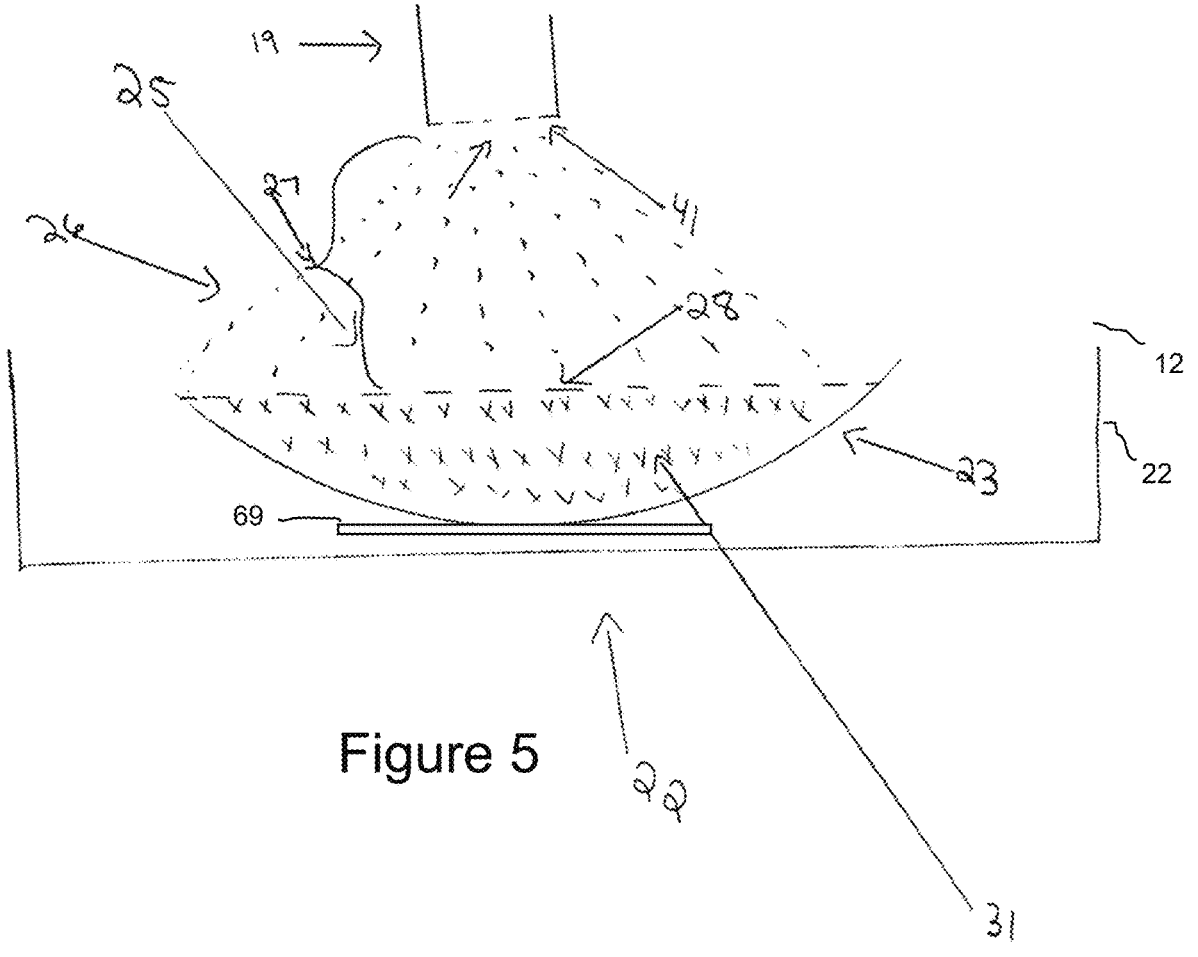
FIG. 5 is a view of the nozzle's spray path onto the receptacle.

As seen in FIGS. 4 and 5, fluid may be drawn from reservoir 17 via a straw (18) that is shaped in a U-shape (78), with a first end (33) set along the bottom (35) of the reservoir space (17). The straw's (18) first end (33) is set perpendicular (42) to the bottom (35) of the reservoir space (17), The straw (18) rises in a first length (36) towards a one-hundred-eighty-degree curve (37) and passes to a second length (38) which terminates at second end (39) to the input (40) of the nozzle (19). The straw's second end (39) and nozzle (19) intersect the bottom (35) of the reservoir space (17) perpendicularly, such that the liquid spray is directed downward from the reservoir (17).

Figure 6:
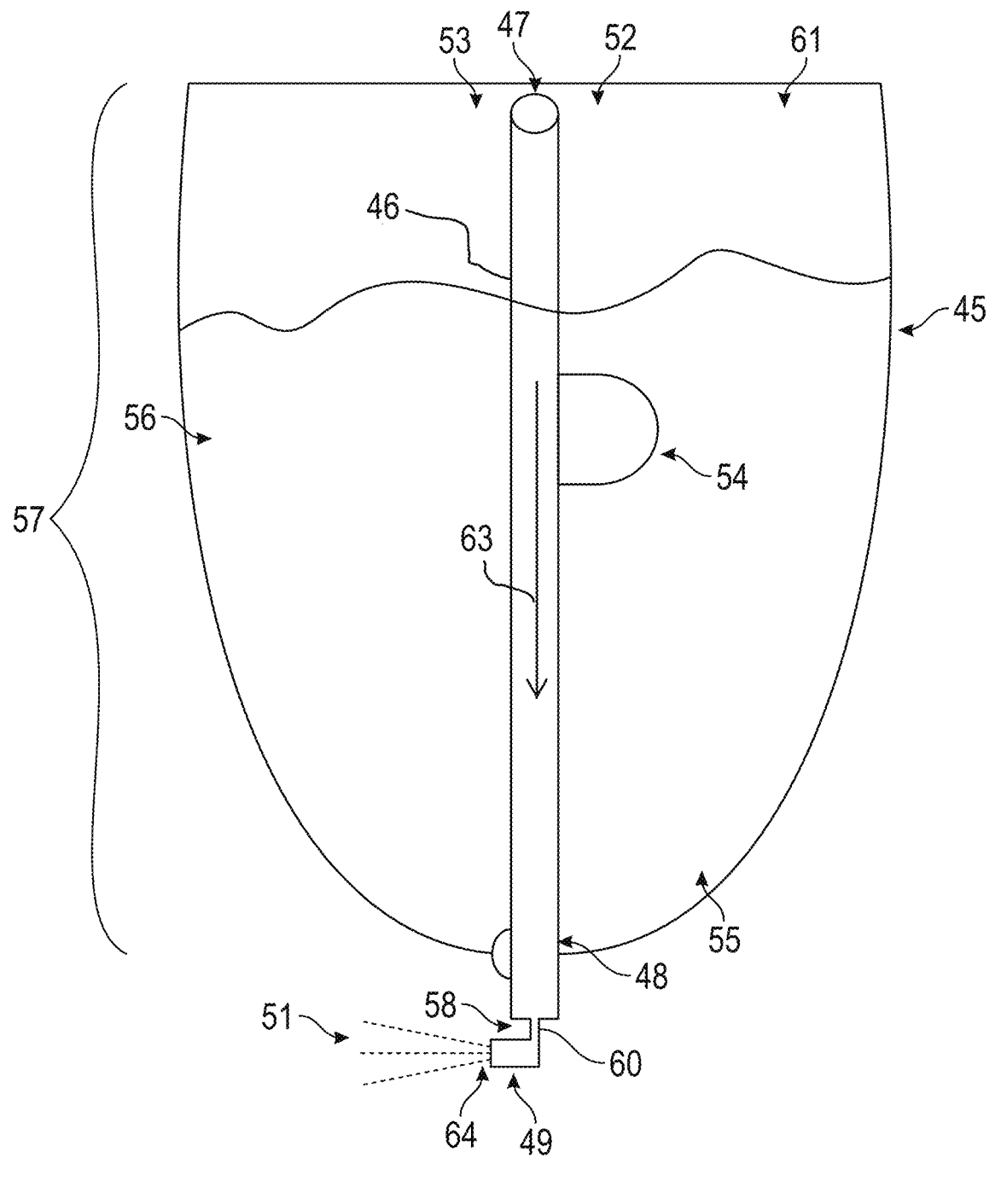
FIG. 6 is a view of spray mechanisms known in the art.

The straw (18) design incorporated into the fragrance unit (9) offers a significantly improved design over that of traditional fragrance spray bottles (45). As seen in FIG. 6, known art fragrance spray bottles use straws (46) that siphon liquid from the first end (47) of the straw to the terminal end of a straw (48) in a straight line. The first end is situated perpendicular to the one side of the spray bottle (53). The straw (46) continues in a straight line, without any change in angle (54), to the spray release side (55) of the spray bottle. The straw may continue, again in a straight line without any angle change (63), into the nozzle input (58). When (a) the bottle is upside down (57) (as is necessary for use in the fragrance unit (9)) and (b) the bottle is not completely full, the liquid's meniscus (59) is below the first end of the straw (47). Such a configuration does not allow for liquid (56) to enter the straw (46). Only air will pass through when the spray release mechanism (60) is triggered. In contrast, because the present invention relies on a "U" shaped straw, the straw is always submerged in liquid when the spray bottle is turned upside down (62), as is necessary for use in the fragrance unit (9).

Additionally, the nozzle (19) disclosed in the present invention offers a significant advantage over known art air freshener nozzles (49). Traditional nozzles (49) are fashioned in an L shape, ending ninety degrees from the nozzle input (58), with spray faces lying in a perpendicular plane to that of the bottom of the receptacle (53). Thus, the spray path of the liquid (51) is rotated 90 degrees from the orientation of the bottle. In the present invention, the spray nozzle is situated, such that the spray nozzle face lies in a plane parallel to the bottom of the reservoir (35). Thus, the spray (21) is discharged normal to the horizontal plane of the spray bottle (66), and normal to the horizontal plane on the receptacle (28).

The nozzle (19) serves to direct fluid downwards onto the receptacle, and may include aperture(s) (41) that may be shaped, or otherwise designed to cause a specific pattern to be set upon the receptacle (23). The receptacle is housed in the bottom compartment of the housing unit (22), on a parallel plane to that of the spray nozzle face. Thus, the spray is emitted downward from the nozzle face (64) onto the receptacle. As seen in FIG. 5, it is preferred that the spray pattern from the nozzle (19) capture as much of the surface area (25) of the top of receptacle (23), without extending the spray pattern (26) beyond the limits of the receptacle surface (23). While the fragrance unit is in the system, it may experience drafts or horizontal winds that can alter the spray pattern between the nozzle (19) and receptacle surface (23) in the distance (27) between the nozzle and receptacle (22). Therefore, the spray pattern may be narrowed to prevent overspray at the expense of spraying the entire receptacle surface. The nozzle may be joined to an adjuster (44) that allows users to adjust the aperture (41) size, thereby limiting the spray pattern to land only on the receptacle surface (23). Given that the fragrance unit is intended to be three hundred sixty degree symmetrical, the spray pattern and receptacle are preferably circular in shape, and the spray pattern is limited towards edges in all directions along the horizontal plane (28) of the receptacle surface (23).

When the spray release mechanism (30) is triggered, the liquid (20) is siphoned through the curved straw (18), out through the nozzle (19). The curved straw (18), has a first end (33) set along the bottom (35) of the reservoir space (17). Straw rises in a first length (36) towards a one-hundred-eighty-degree curve (37) and passes to a second length (38), terminating at a second end (39) to the input (40) of nozzle (19). Both straw ends (33, 39) run perpendicular to the bottom of the reservoir (25). Such a configuration siphons liquid from the bottom of the reservoir (25), providing a flow path for the last drops of liquid in the reservoir (17).

As seen in FIG. 5, the reservoir (17) can be encapsulated in a rigid outer casing (24), such that when the reservoir is forced against the casing (24) the pressure compresses the spray release mechanism (30). The spray release mechanism (30) may be a positive displacement pump such that compressing the spray release mechanism (30) forces liquid out of the nozzle (19).

Alternatively, as seen in FIG. 4, the spray release mechanism (30) can be activated without forcing the entire reservoir (17) against a rigid outer casing (24). Rather an actuator (13) can directly trigger the spray release mechanism (30), forcing the liquid (20) to spray downward out of the nozzle's apertures (41). Other examples of spray release mechanisms include, but are not limited to, spouts that rely on gravity to siphon liquid through the curved straw and out through the nozzle, and air bulb pumps that first suction liquid out of the curved straw, and subsequently force the liquid to spray out of the nozzle (18).

A control system (50) such as a button, dial, switch, remote control, or electronic control panel may control the fragrance unit (9). The control system (50) may be a power switch that powers the unit on and off. Preferably, the control system (50) also allows users to adjust the amount of vapor (29) released by the fragrance system (9). The control system (50) activates an actuator (13), which then compels the spray release mechanism (30) to force the nozzle (19) to spray the liquid (20) out of its apertures (41), and downward into the receptacle (23). The frequency at which the actuator (13) triggers the spray release mechanism (30) is determined by the selected quantity of vapor programmed into the control. The actuator may be powered by a battery (14) or other power source. Alternatively, the actuator (13) may be manually triggered. The actuator may be a motor (13) that drives the spray release mechanism (30) to force the nozzle (19) to spray the liquid (20) into the receptacle (23). The actuator (13) can also be attached to one or more gears (16) that either press down on the reservoir (17), or directly press on the that direct the spray release mechanism (30) to force liquid (20) to spray out of the nozzle (19). Alternatively, the actuator (13) may be attached to a system of pulleys (16) that similarly trigger the spray release mechanism. The system may include a timer for periodic release of fragrance oils onto the receptacle. Alternatively, the receptacle may be placed upon a weight scale 69 to determine the weight of oils on the receptacle (pad) and thereby release more fragrance oil from reservoir to receptacle when the weight is below a minimum. Alternatively, the system may be tied to the automatic, or powered fan unit of the forced air system to begin periodic spraying of oils onto receptacle when the fan is running, and to pause, or sleep when the A/C fan is off. Alternatively, the system may include a wind/air motion sensor 70 on the external portion of housing that can trigger upon the activation of the distribution fan and thereby trigger release, or periodic release of fragrance oil onto receptacle. Preferably there are a plurality, at least three, sensors 70 to allow the vertically symmetrical unit to be placed in any orientation, preferably on a flat horizontal surface, such that no matter the horizontal or other directional air flow, the senores will notice the wind activity (and potentially direction thereof).

As seen in FIG. 1, the housing has a removable top cover (12), such that the reservoir is easily accessible when the cover is detached. The cover (12) may be screwed on and off, popped on and off, attached with clips, or removed in any other non-damaging fashion. The cover may or may not be vented. When users need to replace the liquid, either because the reservoir is empty, or because a different vapor is desired, the cover (12) can be detached, such that the reservoir (17) can be removed and replaced. The system (9) may work with both disposable and washable/refillable reservoirs (17), therefore the interior of the reservoir may be coated with a super hydrophobic and oil repelling material, such as polytetrafluoroethylene or other fluorocarbon. Such coatings facilitate easily emptying, washing, and refilling the container with the user's liquid of choice.

Additionally, to prevent the liquid (20) from reacting with the reservoir (17) and curved straw (18), the reservoir (17), the nozzle input (40), and the nozzle (18) may be fashioned from non-reactive materials including, but not limited to, non-reactive metals (such as stainless steel), silicone, and glass. While other, more cost effective, materials like plastics and aluminum are sufficient stainless steel, glass, and silicone are chemically resistant, and less likely to be contaminated.

The fragrance unit (9) is intended to be self-contained, and mess free. Therefore, it is essential that the spray pattern (26) be entirely contained onto the receptacle (23). The spray pattern (26) must be one that does not approach the housing vents (11), but rather one that entirely remains within the confines of the receptacle. Additionally, the liquid should remain trapped within the confines of the receptacle (23) indefinitely. In order to prevent the liquid from seeping out of the receptacle (23), the receptacle (23) may be composed of a porous material that will properly contain all of the liquid spray (21). Such suitable materials include, but are not limited to, cotton, wool, microfiber, and other absorbent/hydrophilic materials. The receptacle may also be a sponge or absorbent pad. When the receptacle becomes too soiled to absorb liquid, or when users want to change the vapor (29) evaporating from the fragrance unit (9) the bottom compartment can be separated from the housing. The receptacle (9) can then be removed and replaced with either a new receptacle or with a clean, washed receptacle. The fragrance unit (9) is intended to be three-hundred-sixty-degree symmetrical, therefore the receptacle (23) is preferably circular in shape. The horizontal plane of the receptacle surface (28) lies parallel to the horizontal plane of the nozzle spray face (64).

Alternatively, the receptacle may be a non-porous container with a vented lid, configured in a way that provides a path for all of the spray to enter the container, while ensuring that liquid cannot escape through the vents.

As seen in FIG. 3, After the receptacle (23) is impregnated with the spray (21), the low-pressure environment enables the permeated liquid (31) to begin evaporating, as vapor (29), out of the receptacle (23), and out of the housing (10) through the vents (11). The housing (10) has a plurality of vents (11) on the bottom compartment, such that the vapor (29) can easily diffuse out of the housing (10) and into the HVAC distribution system. When the fragrance system (9) is placed between the return (15) and fan (26) of an HVAC system, the flow path of the vapor (32) will be determined by the fan (26) of the HVAC system. Namely, the vapor will flow away from the housing (10) towards the fan (26), and then through the system of ducts (128). The pressure in the ducts (128) may be adjusted to ensure adequate airflow. The vapor will travel through the ducts (128), and continue circulating, ultimately dispersing via the supply vent (34).

The fragrance unit (9) should be placed on a flat, solid surface (68) between the air return and fan of a forced air conditioning system. The control (50) should then be powered on, and set to release the desired concentration of vapor (29). When the vents (67) of the air return are open, and the blower fan (26) is on, the blower fan (26) draws air into the return vents and funnels it through the ducts of the HVAC system. Thus, the space between the air return (15) and fan (26) is one of relatively low air pressure. Due to the Bernoulli principle, the low air pressure coupled with the convection created by the fan will enable the liquid spray (21) absorbed by the receptacle to evaporate off of the receptacle (17) out through the housing vents (11). The housing vents (11) may be located on the bottom compartment (22), on the bottom (22) and top (12) compartments, or throughout the housing (10). The vapor then follows the flow path of the fan (26) into the distribution path ducts (128), ultimately dispersing out of the distribution path through the open supply vent (34). The distribution path may be a single, or series of ducts where convection drives the vapor's distribution. The distribution path may be indoors or outdoors.

The fragrance unit may be used to distribute various vapors through a distribution path. For example, the system can be used to distribute fragrance, disperse air freshener, or to aromatize a space. Alternatively, the system can be used to spread poison or irritants as a method for fumigating for rodents and pests. The system can also be used to remotely distribute a pharmaceutical compound to a patient. As should be apparent from above, regardless of which liquid users choose to disperse via the present invention, the system is distinguishable in its ability to disperse vapor without dirtying the HVAC system and system filters.

I claim:

1. An apparatus for the distribution of airborne particulates or particles or gases or vapors as distributable material, said apparatus comprising:
   a. a unit comprising a housing comprising a reservoir of distributable material;
   b. said unit housing further comprising at least one aperture for dispersion of said distributable material from said unit;
   c. wherein said reservoir includes a curved straw with a first end submerged in said reservoir, said curved straw rises in a first length towards a one-hundred-eighty-degree curve in an inverted U-shape within the reservoir, said curved straw passes to a second length which terminates at a second end, wherein the first end is set above the second end, said curved straw further comprising a nozzle directing flow to a receptacle in a lower compartment of said unit, said lower compartment being directly below said reservoir, said lower compartment in fluid communication with said aperture.

2. The apparatus of claim 1 comprising a drive mechanism to force particulates or particles or gases or vapors out of said unit from said receptacle through said aperture.

3. The apparatus of claim 2 wherein said nozzle is downward facing and directs flow downwards into said receptacle.

4. The apparatus of claim 3 wherein said receptacle is an absorbent pad located said lower compartment of said unit.

5. The apparatus of claim 1 wherein said first end is perpendicular to a bottom of the reservoir.

6. The apparatus of claim 5 wherein said receptacle is placed on a parallel plane to a bottom of said reservoir; and wherein said spray nozzle comprises a face that lays parallel to said parallel plane of said reservoir; and said lower compartment has at least one aperture vent.

7. The apparatus of claim 1 wherein said housing is placed in a low-pressure space of a forced air conditioning system.

8. The apparatus of claim 7 wherein said forced air conditioning system is connected to a series of ducts defining a distribution path of dispersed material.

9. A method of distributing airborne particulates or particles or gases or vapors from a unit, said method comprising the steps of:
   a. drawing a material from a reservoir of liquid within a housing via a curved straw with an inverted U-shape with a first end submerged under a surface of the liquid in the reservoir, a curved top within the reservoir, and a second end comprising a downward facing nozzle below the reservoir;
   b. forcing the material through the nozzle onto a receptacle directly below the reservoir of liquid; and
   c. driving the material out of the unit.

10. The method of claim 9 whereby said step of forcing is conducted by an actuator.

11. The method of claim 9 whereby said step of driving causes evaporated material to exit the unit.

12. The method of claim 9 whereby said step of forcing directs a spray downward onto an absorbent pad located in a bottom compartment of the unit.

13. A method for spreading vapor, the method comprising:
   placing a liquid reservoir in a low-pressure system;
   releasing the liquid through an inverted U-shaped curved straw passing within the liquid reservoir through to a flow path exiting from the reservoir to a nozzle directly below the liquid reservoir;
   channeling the liquid from a downward spray onto a receptacle;

setting a low pressure around a housing to cause evapo-
rated vapor from the liquid in the receptacle to exit the
receptacle; and spreading the vapor through a distribution path;

wherein the inverted U-shaped curved straw includes a
first end in the reservoir and a second end in a recep-
tacle and wherein the second end is set below the first
end.

14. The method according to claim 13 wherein the low-
pressure system is produced between an air return a circulation fan of a forced air conditioning system.

15. The method according to claim 13 further comprising
the step of compelling flow of the liquid through the inverted
U-shaped curved straw via an actuator.

16. The method according to claim 13 whereby the liquid
evaporates from the receptacle out through an aperture in the
housing.

17. The method according to claim 13 wherein the dis-
tribution path is a duct or series of ducts.

18. The apparatus of claim 1 further comprising an
actuator providing force to cause fluid to pass through the
nozzle.

* * * * *